United States Patent [19]

Bassen et al.

[11] Patent Number: 5,678,550
[45] Date of Patent: Oct. 21, 1997

[54] APPARATUS AND METHOD FOR IN SITU DETECTION OF AREAS OF CARDIAC ELECTRICAL ACTIVITY

[75] Inventors: Howard Bassen, Chevy Chase; Victor Krauthamer, Wheaton, both of Md.

[73] Assignee: The United States of America as represented by the Secretary of the Department of Health and Human Services, Washington, D.C.

[21] Appl. No.: 513,713

[22] Filed: Aug. 11, 1995

[51] Int. Cl.$^6$ ............................................ A61B 5/00
[52] U.S. Cl. .................... 128/654; 128/656; 128/634; 128/664; 128/665
[58] Field of Search ............................. 128/654, 656, 128/633, 634, 658, 664, 665

[56] References Cited

U.S. PATENT DOCUMENTS

| | | |
|---|---|---|
| 4,768,513 | 9/1988 | Suzuki . |
| 4,785,806 | 11/1988 | Deckelbaum . |
| 5,029,331 | 7/1991 | Heichler et al. . |
| 5,227,308 | 7/1993 | Jameson et al. . |
| 5,239,998 | 8/1993 | Krauthamer . |
| 5,273,041 | 12/1993 | Richards et al. . |
| 5,309,907 | 5/1994 | Fang et al. . |
| 5,421,337 | 6/1995 | Richards-Kortum et al. . |
| 5,421,339 | 6/1995 | Ramanujam et al. . |

OTHER PUBLICATIONS

Krauthamer, Victor *In Vitro Toxicology*, 6, 109–116 (1993).
Haugland, R.P. "Handbook of Fluorescent Probes and Research Chemicals" 5th Ed., Molecular Probes, Inc., 153–158 (1992).

Montana et al., *Biochemistry*, 28, 4536–4539 (1989).
Ross et al., *Journal of Neuroscience*, 4, 659–672 (1984).
De Weer et al., "Optical Methods in Cell Physiology," *Society of General Physiologists and Wiley–Interscience*, 40, 71–99.
Krauthamer V., Bryant, H.J. et al., *Journal of Fluorescence*, 1, 207–213 (1991).
Kudo, Y., Takeda, K. et al., *J. Neuroscience Methods*, 30, 161–168 (1989).
Dillon, S.M. and Wit A.L., *Proc. IEEE–BME*, 10, 215–216 (1988).

*Primary Examiner*—Marvin M. Lateef
*Assistant Examiner*—Shawna J. Shaw
*Attorney, Agent, or Firm*—Townsend and Townsend and Crew and; Guy W. Chambers

[57] ABSTRACT

An apparatus and method for detecting electrical activity in areas of tissue. The apparatus (1) includes a main catheter (5), multifibered endoscope (10), light filtering means (30, 42, 52), photodetectors (40, 50) and a signal processor (60). The apparatus is used to detect electrical activity by first infusing both an electrically sensitive dye and an electrically insensitive reference dye into the subject tissue and then detecting the intensity of light emitted from both dyes. The wavelength of light emitted from each dye is different. The intensity of light emitted from each dye is similar for non-electrically active tissue and moving tissue but different for electrically active tissue. The intensity of light from the two dyes as separately recorded by the photodetectors is compared by a signal processor to eliminate noise attributable to movement within the area of tissue and arrive at a accurate calculation of electrical activity within the area of tissue.

22 Claims, 3 Drawing Sheets

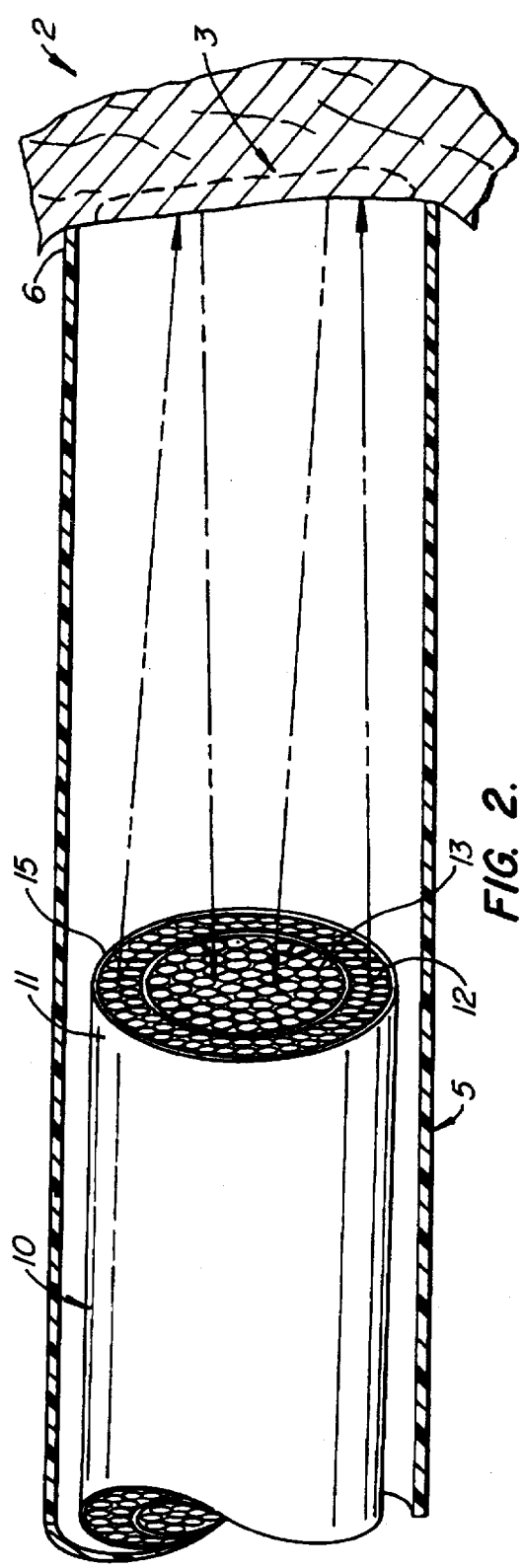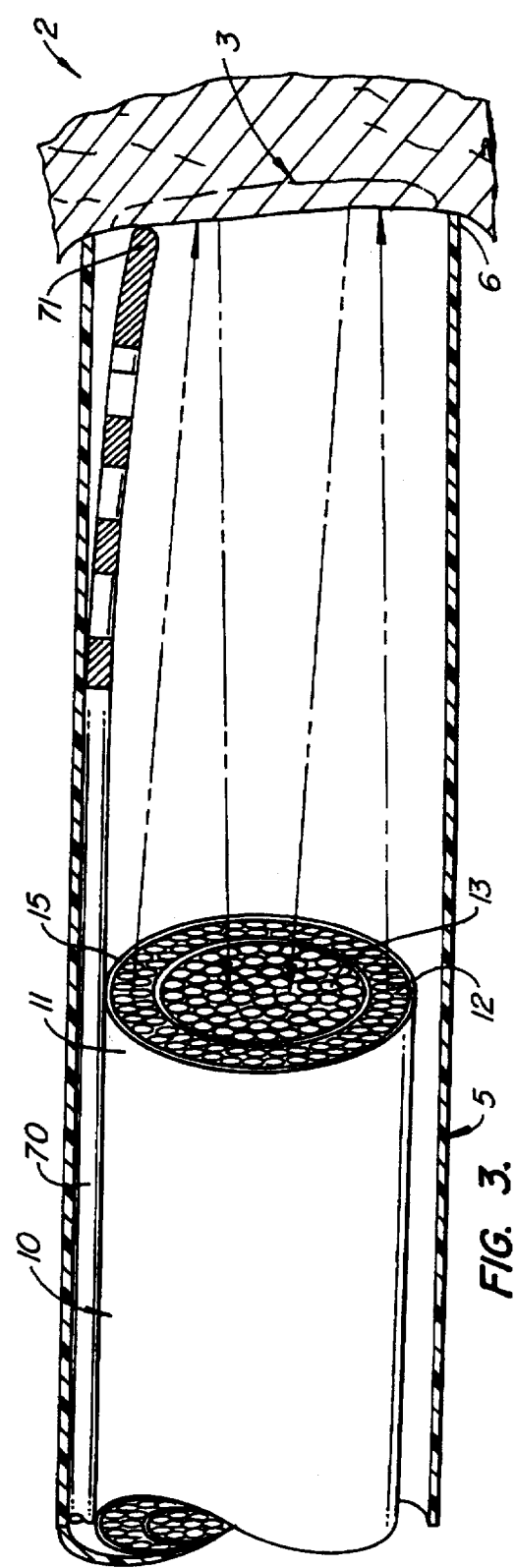

APPARATUS AND METHOD FOR IN SITU DETECTION OF AREAS OF CARDIAC ELECTRICAL ACTIVITY

TECHNICAL FIELD OF THE INVENTION

The present invention relates to the in situ detection of electrical activity in areas of cardiac and other electrically active tissue. More particularly, the present invention features a multifibered endoscope and multiple tissue dyes to detect accurately electrical activity over an area of electrically active tissue.

BACKGROUND OF THE INVENTION

Optical recording has, for some time, been a means of detecting the electrical activity of human cells. In cardiac applications, determining the electrical activity of heart tissue is often a necessary prerequisite to the identification and treatment of abnormal electrical rhythms. Currently, over 400,000 people in the United States die each year from heart problems, including those caused by abnormal electrical rhythms.

Most optical recording techniques require the use of electrically sensitive dyes which bind to cell membranes and respond linearly to changes in cellular electrical activity by emitting fluorescent light at different intensities. Specifically, an electrically charged cell membrane dyed with an electrically sensitive dye will emit fluorescent light at a different intensity than an electrically uncharged cell membrane dyed with the same dye. By comparing the intensity variations of emitted fluorescent light from dyed cells, one can determine which cells are electrically active and which cells are not.

The standard method for optically recording electrical activity of cellular tissues stained with electrically sensitive dyes involves the use of microscope optics. Nonetheless, this method is limited because it requires a clear line-of-sight path between the required light source, the tissue under investigation and the light detector. To provide this necessary clear line-of-sight path, extensive surgical dissection of the tissue is often required. Accordingly, this line-of-sight method is often impractical to use in situ, particularly in cardiac applications.

More recent work with optical fibers has made in situ optical recording possible. Dillon, for example, was the first to perform in vivo recording using a fluorescent dye system in which excitation light was emitted from one optical fiber to stimulate fluorescent emissions from the dyed tissue which could be detected from a concentric bundle of fibers. Dillon, S. M. and Wit A., "Use of Voltage Sensitive Dyes to Investigate Electrical Defibrillation", *Proc. IEEE-BME*, 10:215-216.

Kudo has also worked with optical fibers to optically record the electrical activity of tissues. Kudo et al., "A New Device for Monitoring the Concentration of Intracellular $Ca^{2}$—in CNS Preparations and its Application to the Frog Spinal Cord", *J. Neuroscience Methodology*, 30:161-168. In his apparatus, Kudo used two fibers in a micropipette, one for exciting fluorescence in tissue from a calcium-sensitive dye and the other for detecting fluorescence.

A compact apparatus that is particularly suitable for use in situ is disclosed in co-inventor Krauthamer's U.S. Pat. No. 5,239,998. In that patent, an apparatus is disclosed which allows excitation of fluorescent dyed tissue and detection of changes in fluorescence by the same optical fiber.

While these prior art approaches have contributed to making optical recording of electrical activity in situ with optical fibers possible, each of these approaches is limited to a point-by-point analysis of electrical activity. To the extent electrical activity needs to be mapped over an area of tissue, such as to identify a specific area of tissue responsible for aberrant electrical activity in the heart, use of the prior art approaches would involve a time consuming and laborious process of mapping one point at a time. To the extent such prior art mapping techniques are done in situ in cardiac tissue, the risk to the patient increases with the amount of time the apparatus needs to be left in the body.

One problem with using electrically sensitive dyes to detect electrical activity over an area of tissue is that movement of the tissue during the measurement process can destroy the accuracy of such measurements. Specifically, tissue movement can create variations in the intensity of emitted light which mimic the variations in intensity created by electrical activity within the tissue. As such, it is impossible to differentiate whether the intensity detected from the dyed tissue is due to cellular electrical activity or to tissue movement. In the prior art, this problem is most often addressed by providing motion inhibiting drugs. As with other type of drugs, though, these motion inhibiting drugs can have deleterious side effects.

The prior art also fails to provide a means to infuse liquids into the tissue sample, obtain electrical readings and perform corrective surgery all in one apparatus. Typically, the prior art would require successive insertions of a catheter, endoscope and ablation apparatus to perform all these functions. The successive insertions of all these apparatuses into a patient is not only a complicated process but also increases the possibility of the various apparatuses misaligning and thereby creating potentially disastrous results (e.g., if healthy heart tissue is inadvertently ablated due to misalignment).

SUMMARY OF THE INVENTION

The present invention provides an apparatus and method for detecting electrical activity in areas of tissue. The apparatus includes a main catheter, multifibered endoscope, light filtering means, photodetectors and a signal processor. The multifibered endoscope, in its preferred form, has an outer ring of optical fibers to transmit light to an area of the subject tissue and an inner, concentric bundle of optical fibers to detect fluorescent light which is emitted from the same area of the subject tissue. Fluorescent light is emitted from the subject tissue at two different wavelengths, one wavelength characteristic of an electrically sensitive dye infused through the catheter into the subject tissue and another wavelength characteristic of a non-electrically sensitive reference dye also infused through the catheter into the subject tissue. The intensity of fluorescent light emitted at each of the two wavelengths is similar for non-electrically active tissue and moving tissue but different for electrically active tissue. An optical enhancing solution is preferably used during operation of the endoscope to improve the reliability of the data received. After the two wavelengths of fluorescent light are received by the bundle of optical fibers, the two wavelengths are separated by a dichroic beamsplitter. Aberrant light is then filtered and the intensity of light at each wavelength is detected by respective photodetectors. The intensity of fluorescent light from the two dyes as recorded by the respective photodetectors is then compared by a signal processor to eliminate noise attributable to movement within the area of tissue and arrive at an accurate calculation of electrical activity within the area of tissue.

In an alternative embodiment, the multifibered endoscope of the present invention is attached to an ablation catheter and housed, with the ablation catheter, within the main catheter in order to allow the prompt and accurate infusion of fluids, detection of areas of electrical activity and ablation of undesired tissue.

BRIEF DESCRIPTION OF THE DRAWINGS

FIG. 2 shows a close up view of the distal end of the apparatus shown in FIG. 1.

FIG. 3 shows an alternative form of the apparatus of the present invention which includes an ablation catheter for removing undesired tissue.

DESCRIPTION OF THE PREFERRED EMBODIMENT

Figure 1:
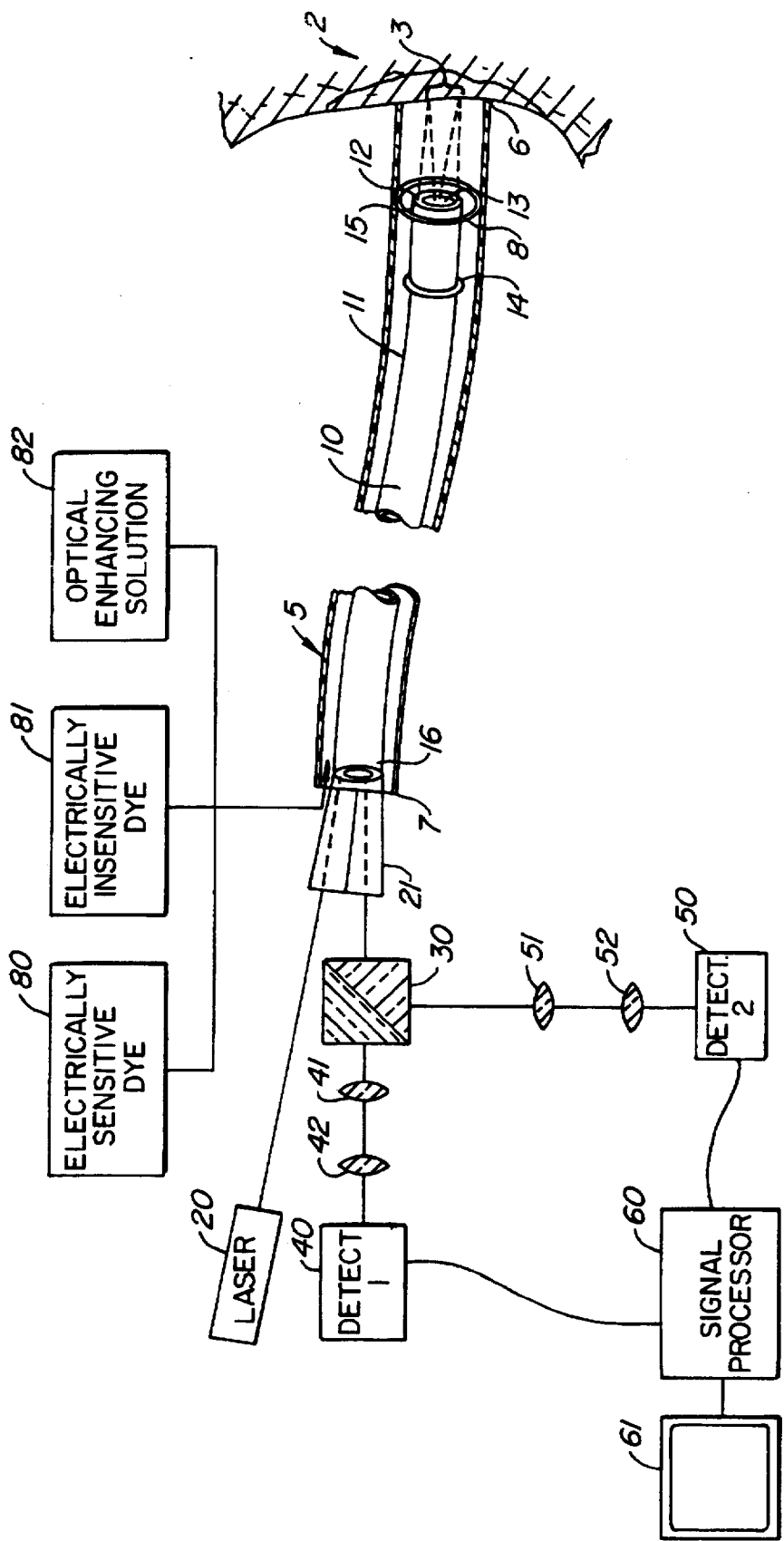
FIG. 1 shows a schematic illustration of a preferred form of apparatus for the present invention.

The present invention provides a means to detect optically electrical activity over an area of tissue, rather than simply at one point at a time. This capability is accomplished through use of multiple dyes, an optical enhancing solution and a specially constructed endoscope apparatus.

The preferred dyes for the present invention are an electrically sensitive dye and an electrically insensitive reference dye. Tissue dyed with both types of dyes will emit light at roughly the same intensity from moving tissue and electrically inactive tissue. By contrast, electrically active tissue will emit light at a different intensity at the wavelength of the electrically sensitive dye than at the wavelength of the electrically insensitive reference dye. By comparing the intensity of light emissions from the two dyes, one can determine the location and electrical activity of the tissue.

Preferred types of electrically sensitive dyes include the styryl voltage sensitive dyes, which are excited by green light at a wavelength of about 490-545 nm and, in response, emit red fluorescence at a wavelength of about 600-700 nm. Suitable styryl voltage sensitive dyes include the Di-4-ANEPPS, RH237 and RH461 dyes produced by Molecular Probes, Inc. of Eugene, Oreg. Other suitable electrically sensitive dyes for use in the present invention are described in Haugland, Richard P., Handbook of Fluorescent Probe and Research Chemicals, pp. 153-158, 5th Ed. (1992-94); Grinvald et al., "Improved Fluorescent Probes for the Measurement of Rapid Changes in Membrane Potential", *Biophysics Journal*, 39:301-308 and Grinvald et al., "Optical Recording of Synaptic Potentials from Processes of Single Neurons using Intracellular Potentiometric Dyes", *Biophysics Journal*, 51:643-651, the disclosures of which are incorporated by reference.

The reference fluorescent dye should be selected not only to be electrically insensitive but also to emit a wavelength that is different from the wavelength emitted by the electrically sensitive dye. For example, if the di-4-ANEPPS dye is chosen as the electrically sensitive dye having an emission of red fluorescence at 664 nm, a suitable reference dye would be the tetramethirohodamine (T1391) dye produced by Molecular Probe, Inc. This T1391 dye can be illuminated by a range of visible wavelengths, including the green light wavelengths (i.e., 490-545 nm) used to illuminate the di-4-ANEPPS electrically sensitive dyes, but would emit fluorescence in a different wavelength, namely a yellow-green fluorescence at 570 nm.

While the preferred embodiment of the present invention involves the use of one electrically sensitive dye and one electrically insensitive reference dye which emit fluorescent light at different wavelengths, those of skill in the art will recognize that the goal of removing movement related noise from electrical activity measurements can be accomplished in similar ways. For example, electrically sensitive and electrically insensitive dyes could be chosen which emit electromagnetic waves outside the visible spectrum. Also, a single dye could be chosen which emits one color of light from electrically active cells and a different color of light from electrically inactive cells.

An optical enhancing solution is preferably used during endoscope operation. This optical enhancing solution prevents illuminating and emitted light from being blocked or diffused by blood cells present in the space between the endoscope and the subject tissue. This optical enhancing solution can be a simple oxygenated saline solution but is more preferably a perfluorochemical emulsion such as the FLUOSOL emulsion produced by Alpha Therapeutic Corp. of Los Angeles, Calif.

Referring now to FIGS. 1 and 2, a preferred form of endoscopic apparatus 1 of the present invention is shown. In this endoscopic apparatus 1, a main catheter 5, having distal 6 and proximal ends 7, is shown housing a multifibered endoscope 10 of the present invention. The main catheter 5 is selected with an outside diameter large enough to allow the multifibered endoscope 10 to easily slide through the inside of the catheter and still have enough extra room to infuse fluids, such as the electrically sensitive dye 80, electrically insensitive reference dye 81 and optical enhancing solution 82. A catheter obtained from Intramedic of Parsippany, N.J. with an outside diameter of 5 mm has been found to be suitable for this purpose. The main catheter 5 should be sufficiently long so that the distance between its distal end 6 and proximal end 7 will allow the desired tissue situs to be easily reached as shown, for example, in FIG. 4. For cardiac applications, this length is on the order of about 2 meters.

Toward the distal end 6 of the main catheter 5 is a radiopaque reference marker 8. The reference marker 8 can take the form of, for example, a ring or dot of metal and is preferably embedded within the catheter so as to avoid blood contamination. The radiopaque reference marker 8 is embedded at a predetermined distance from the distal end 6 of the catheter so that the exact in situ location of the distal end 6 of the catheter can be ascertained using X-rays.

The multifibered endoscope 10, having distal 15 and proximal 16 ends, includes a sheathing 11, formed of a pliable, polymeric material, which surround a ring of light transmitting optical fibers 12 and a central bundle of fluorescent light receiving optical fibers 13. The individual optical fibers which make up the ring of light transmitting optical fibers 12 and the core of fluorescent light receiving optical fibers 13 are chosen to have a minimum overall diameter, preferably 140 μm or less. A radiopaque reference marker 14 is preferably embedded toward the distal end 15 of the endoscope so that the in situ location of this distal end 15 can be ascertained using X-rays. A suitable multifibered endoscope for use in the present invention is the AS-2.4-200D endoscope produced by Machida & Co. of Orangeburg, N.Y. Those of skill in the art will, of course, recognize that other types of endoscopes can also be used for the present invention. Such alternative endoscopes include an endoscope where the central bundle of fibers transmits light and the outer ring of fibers receives light, or the single fibered endoscope described in U.S. Pat. No. 5,239,998.

The distal end 15 of the multifibered endoscope 10 is preferably recessed back about 1 cm from the distal end 6 of the main catheter. This recessing back allows the distal end 6 of the main catheter to rest against the subject tissue 2 and spaces the multifibered endoscope far enough away from the subject tissue 2 to allow illumination of a suitable area of tissue.

During operation, the ring of light transmitting optical fibers 12 are illuminated by a light source 20, which preferably takes the form of a pulsing argon laser. Nonetheless, any suitable light/optic system capable of producing a beam of excitation light may be used. This light source 20 provides light of a suitable wavelength to excite fluorescent emissions from a dye-stained tissue 3. When utilizing styryl electrically sensitive dye and tetramethirohodamine (T1391) reference dye to stain the subject tissue 2, a light source 20 is preferably selected to produce blue-green light having a wavelength of about 514 nm. One suitable laser which is capable of producing such green light is a 100 mW Argon laser, Model No. 60B which is produced by American Laser of Salt Lake City, Utah.

After light is emitted from the light source 20, it first travels through a fiber coupler 21 before reaching the ring of light transmitting optical fibers 12. This fiber coupler 21 distributes and focuses the light into each of the individual optical fibers making up the ring of light transmitting optical fibers 12. In a preferred embodiment, the fiber coupler 21 is a Model F-1015 fiber coupler produced by Newport of Fountain Valley, Calif. Once the light passes through the fiber coupler 21 and the ring of light transmitting optical fibers 12, it leaves the endoscope and preferably passes through an optical enhancing solution before illuminating an area of the dyed tissue 3. For cardiac applications, this illuminated area is preferably on the order of 1 square centimeter.

The illuminating light excites the area of dyed tissue 3 to emit fluorescent light at two different wavelengths. This fluorescent light is then detected by the bundle of light receiving optical fibers 13, which are at the center of the endoscope. The fluorescent light is then transmitted back through these light receiving optical fibers 13 and fiber coupler 21 to an angled beamsplitter 30. The beamsplitter 30 is preferably a dichroic filter which transmits light above a certain wavelength and reflects light below that wavelength. If, in the case of the preferred example, a styryl di-4-ANEPPS dye is used as the electrically sensitive dye (i.e., 664 nm emission), T1391 is used as the reference dye (i.e., 570 nm emission) and blue-green light (i.e., 514 nm) is transmitted from the light source 20, a suitable beamsplitter 30 would be a dichroic filter which transmits light above 600 nm and reflects light below 600 nm. A dichroic beamsplitter of this type can be purchased from Omega Optical of Brattleboro, Vt.

Two lens 41 and 51 are interposed between the beamsplitter 30 and each photodetector 40 and 50 to focus the light emanating from the beamsplitter 30. In the case of lens 41, the fluorescent light is focused through one or more filter(s) 42 and into photodetector 40. In order to have photodetector 40 receive only fluorescent light emitted at a wavelength corresponding to the electrically sensitive dye, the filter(s) 42 must remove wavelengths of light corresponding both to the electrically insensitive reference dye and the light source 20. If, again in the case of the preferred example, a styryl di-4-ANEPPS dye is used as the electrically sensitive dye (i.e., 664 nm emission), T1391 is used as the reference dye (i.e., 570 nm emission) and blue-green light (i.e., 514 nm) is transmitted from the light source 20, the 600 nm dichroic beamsplitter 30 will have theoretically removed the unwanted light originating from the reference dye and light source. In this case, the filter 42 can be a single 664 nm band-pass filter which serves to better insure that only fluorescent light corresponding to the electrically sensitive dye is received by the photodetector 40.

In contrast to photodetector 40, reference photodetector 50 is intended only to collect fluorescent light emitted by the electrically insensitive reference dye. If, again in the case of the preferred example, a styryl di-4-ANEPPS dye is used as the electrically sensitive dye (i.e., 664 nm emission), T1391 is used as the reference dye (i.e., 570 nm emission) and blue-green light (i.e., 514 nm) is transmitted from the light source 20, filter(s) 52 is needed to filter out the transmitted blue-green incident light which was also reflected from the angled 600 nm beamsplitter. This filter(s) 52 could, in this example, take the form of a single 540 nm high pass interference filter, a single 570 nm bandpass filter or both filters. Suitable filters for use in the present invention can be obtained from a variety of sources known to those in the art, including Omega Optical of Brattleboro, Vt. and the Oriel Company of Stratford, Conn.

After the intensity of light from both the electrically sensitive and electrically insensitive reference dyes are sensed by photodetectors 40 and 50, respectively, this information is passed along in real time to signal processor 60. It is the function of the signal processor to first discount any portion of the signal from the electrically sensitive dye which is attributable to motion in the tissue. The signal processor does this by taking a ratio of its time dependent signal from the electrically sensitive dye to its time dependent signal from the electrically insensitive reference dye according to the following equation:

$$R = \frac{\Delta F_1/F_1}{\Delta F_2/F_2}$$

In this equation, R is the resulting electrical activity in the probed area of the heart, $\Delta F_1$ is the change in intensity of the electrically sensitive dye during an incremental time period, $F_1$ is an average value of intensity of the electrically sensitive dye during that incremental time period, $\Delta F_2$ is the change in intensity of the electrically insensitive reference dye during the same incremental time period and $F_2$ is an average value of intensity of the electrically insensitive reference dye during that same incremental time period. For purposes of this equation, the incremental period of time is preferably on the order of 1 millisecond. If desired, the resulting electrical activity in the probed area of the heart can be displayed in time graph form on a display monitor 61 or recorded by other means known to those in the art.

FIG. 3 shows an alternative embodiment of the present invention which includes an ablation catheter 70, having an ablation electrode at its distal end 71. This ablation catheter is preferably affixed to the sheathing 11 of the endoscope 10 and fitted, along with the endoscope 10, inside the main catheter 5. In cardiac applications, this ablation catheter 70 allows the tissue responsible for abnormal electrical rhythms to be removed as soon as it is identified by the endoscopic apparatus 1. A preferred form of ablation catheter for the present invention is the Cardiorhythm RF Mariner ablation catheter produced by Medtronic, Inc. of Minneapolis, Minn.

Figure 4:
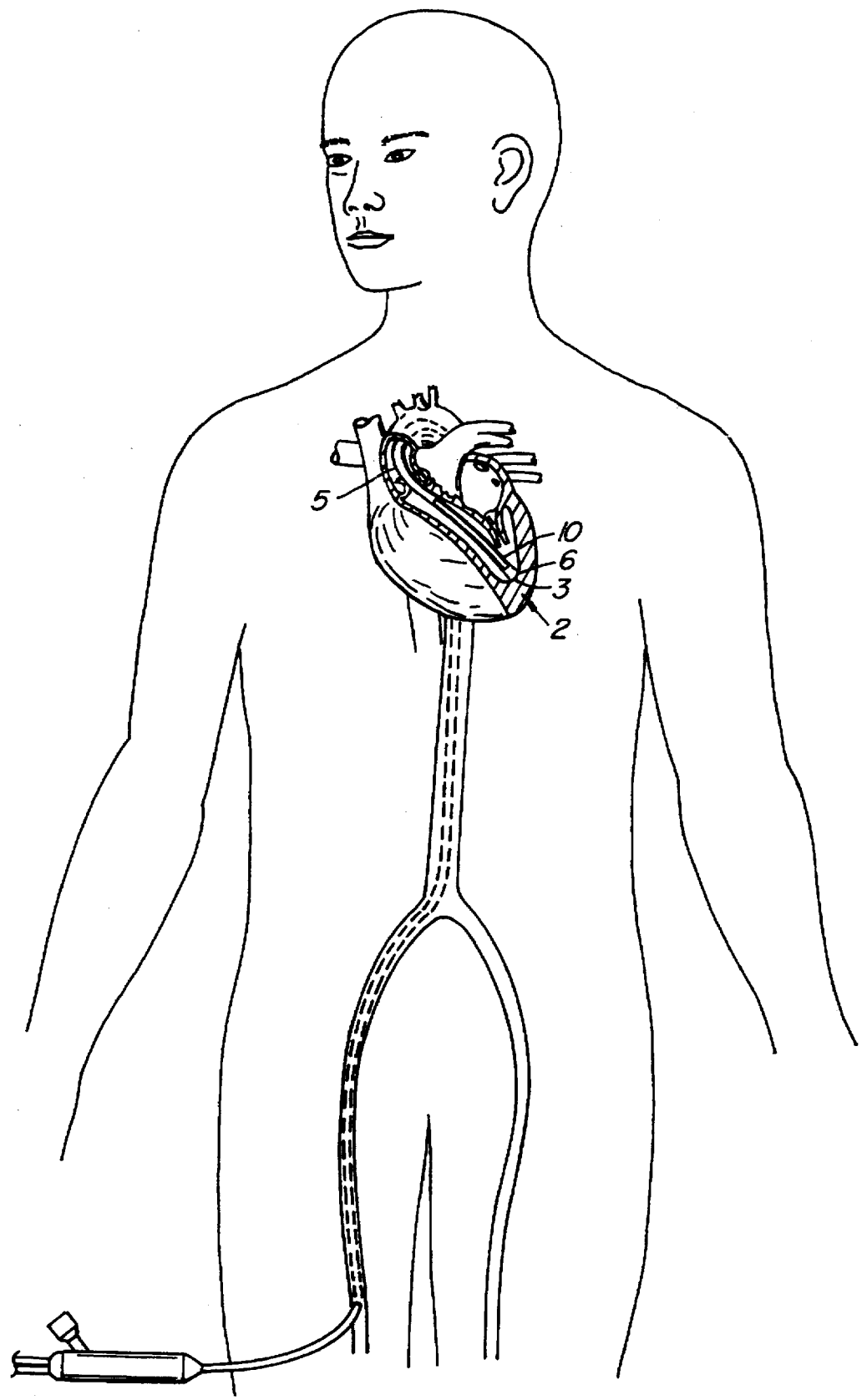
FIG. 4 shows a multifibered endoscope of the present invention in operation for a cardiac application.

Referring to FIG. 4, to use the multifibered endoscope 10 of the present invention to monitor in situ the electrical activity of heart tissue, an opening is first made in the skin of the patient which is large enough to allow the multifibered endoscope and suitable catheters to pass through. If, for example, it is desired to survey the electrical activity of the left ventricle of the heart, a syringe would typically be inserted into the leg of the patient until it reaches the femoral artery. An introducer sheath (not shown) is then inserted into the hole created by the syringe to allow the main catheter 5 to be inserted.

After insertion through the introducer sheath, the main catheter 5 is threaded through the femoral artery, aortic arch and left ventricle of the heart until its distal end 6 reaches the left coronary artery. As previously noted, the position of the distal end of the main catheter 6 can be tracked by taking X-rays and checking for the position of the metal reference marker. Once the catheter reaches an appropriate position in the coronary artery, the electrically sensitive and electrically insensitive dyes can then be infused through the catheter and into the tissue to be surveyed. The dyes can either be infused sequentially or simultaneously. In the preferred embodiment, the dyes are mixed and infused together so that they will penetrate into the heart tissue in a similar manner.

A dye concentration in the blood of about 42 μm is preferred. To achieve this concentration, the dyes received from the manufacturer (e.g., Molecular Probe Inc.) must typically be dissolved and diluted. Appropriate solutions for dissolving and diluting these dyes include saline, ethanol and DMSO solutions. The inventors have found that a dose of about 1.0 ml at an injected concentration of about 4.2 μM is suitable for infusing the two dyes in cardiac applications. Typically, the dyes will infuse into the subject heart tissue within about a minute.

After the two fluorescent dyes have been infused into the left ventricle of the heart from the coronary artery, the distal end 6 of the main catheter is withdrawn from the coronary artery back into the left ventricle. By checking the location of the metal reference marker with X-rays, the distal end 6 of the main catheter is positioned in the left ventricle at an area where electrical activity is desired to be detected. The distal end 6 of the main catheter is preferably allowed to rest lightly against the area of inner heart wall to be surveyed.

To the extent that the multifibered endoscope 10 has not yet been inserted into the main catheter 5, it is now inserted into the proximal end of the main catheter and pushed through the main catheter until its distal end reaches the left ventricle of the heart. The distal end of the endoscope can be properly aligned in a slightly recessed position (i.e., about 1 cm) with the distal end 6 of the main catheter by using X-rays to exactly position the metal reference markers of the endoscope and main catheter.

Once the multifibered endoscope 10 has been properly positioned within the main catheter 5, an optical enhancing solution is infused through the annular space between the multifibered endoscope 10 and the inside surface of the main catheter 5 so that it fills the viewing space between the multifibered endoscope 10 and the subject tissue 2. This infusion should be continuous during the detection phase at a level of about 0.1 ml per minute.

Endoscope detection in a particular area of the heart should continue until the data collected becomes consistent and reproducible. The endoscope 10 can then be moved to a different area of the heart for further data collection, if desired. If an area of abnormal electrical activity is identified during this detection phase, it is sometimes desirable to try to correct the abnormal electrical activity by ablating the heart tissue responsible for the abnormality. One way to accomplish this ablation is by first removing the multifibered endoscope 10 from the main catheter 5 and replacing it with an ablation catheter (not shown). Nonetheless, this procedure risks ablating the wrong tissue if there is any change in alignment of the main catheter 5 during the time the multifibered endoscope 10 is replaced in the main catheter 5 with the ablation catheter. A preferred approach for ablation is to use the apparatus shown in FIG. 3 in which an ablation catheter 70 is already affixed to the multifibered endoscope 10 in a position where it can remove undesired heart tissue as soon as that tissue is detected by the multifibered endoscope.

In the foregoing specification, the invention has been described with reference to specific preferred embodiments and methods. It will, however, be evident to those of skill in the art that various modifications and changes may be made without departing from the broader spirit and scope of the invention as set forth in the appended claims. For example, those of skill in the art will readily recognize that the apparatuses of the present invention can be inserted in arteries or veins other than those described in the specific example for either humans or animals. This is particularly true where the electrical activity of different parts of the heart or of different organs are to be surveyed. Also, if minimizing the invasiveness of the electrical detection procedure is not important, the two fluorescent dyes can be infused more directly than through a remotely inserted catheter, for example, by direct application of the dyes with syringes or eyedroppers. Similarly, if minimizing invasiveness is not important, the multifibered endoscope of the present invention can be replaced, for example, with a combination of a direct light source and a line-of-sight detection device (e.g., a microscope). The specification and drawings are, accordingly, to be regarded in an illustrative, rather than restrictive, sense; the invention being limited only by the appended claims.

What is claimed is:

1. Apparatus for detecting the level of electrical activity in an area of living animal tissue comprising:

means for infusing into said living tissue both a electrically sensitive dye and an electrically insensitive reference dye;

means for illuminating said dyed living tissue to cause said dyed living tissue to emit fluorescent light at a first wavelength due to said electrically sensitive dye and simultaneously emit fluorescent light at a second wavelength due to said electrically insensitive reference dye;

means to separately detect the intensity of fluorescent emissions at each of said first and second wavelengths;

processing means to compare the intensity of fluorescent emissions at each of said first and second wavelengths and calculate the electrical activity in said area of living animal tissue in a way which discounts fluorescent intensity signals attributable to tissue movement.

2. The apparatus of claim 1 further including a means for displaying the electrical activity calculated for said area of living animal tissue.

3. The apparatus of claim 1 wherein said means for infusing is a catheter.

4. The apparatus of claim 1 wherein said electrically sensitive dye is a styryl voltage sensitive dye.

5. The apparatus of claim 4 wherein said styryl voltage sensitive dye is di-4-ANEPPS.

6. The apparatus of claim 1 wherein said electrically insensitive reference dye is tetramethirohodamine.

7. The apparatus of claim 1 wherein said means for illuminating said dyed living tissue includes a laser, a fiber coupler and a multifibered endoscope.

8. The apparatus of claim 7 wherein said laser is an argon laser emitting blue-green light.

9. The apparatus of claim 1 wherein said means to separately detect the intensity of fluorescent emissions includes a beamsplitter and two sets of lens, filters and photodetectors.

10. The apparatus of claim 9 wherein one set of lens, filters and photodetectors is used to detect the intensity of fluorescent light at said first wavelength and the other set of lens, filters and photodetectors is used to detect the intensity of fluorescent light at said second wavelength.

11. Apparatus for detecting the level of electrical activity in an area of living animal tissue comprising means for infusing into said living tissue both an electrically sensitive dye and an electrically insensitive reference dye;

means for illuminating said dyed living tissue to cause said dyed living tissue to emit fluorescent light at a first wavelength due to said electrically sensitive dye and simultaneously emit fluorescent light at a second wavelength due to said electrically insensitive reference dye;

means to separately detect the intensity of fluorescent emissions at each of said first and second wavelengths, including a dichroic beamsplitter which transmits light above 600 nm and reflects light below 600 nm, and two sets of lens, filters and photodetectors;

processing means to compare the intensity of fluorescent emissions at each of said first and second wavelengths and calculate the electrical activity in said area of living animal tissue in a way which discounts fluorescent intensity signals attributable to tissue movement.

12. Apparatus for detecting the level of electrical activity in an area of living animal tissue comprising:

means for infusing into said living tissue both an electrically sensitive dye and an electrically insensitive reference dye;

means for illuminating said dyed living tissue to cause said dyed living tissue to emit fluorescent light at a first wavelength due to said electrically sensitive dye and simultaneously emit fluorescent light at a second wavelength due to said electrically insensitive reference dye;

means to separately detect the intensity of fluorescent emissions at each of said first and second wavelengths;

processing means to compare the intensity of fluorescent emissions at each of said first and second wavelengths and calculate the electrical activity in said area of living animal tissue in a way which discounts fluorescent intensity signals attributable to tissue movement, such calculation performed using the following equation:

$$R = \frac{\Delta F_1/F_1}{\Delta F_2/F_2}$$

where R is the electrical activity in the probed area of the heart, $\Delta F_1$ is the change in intensity of the electrically sensitive dye during an incremental time period, $F_1$ is an average value of intensity of the electrically sensitive dye during that incremental time period, $\Delta F_2$ is the change in intensity of the electrically insensitive reference dye during the same incremental time period and $F_2$ is an average value of intensity of the electrically insensitive reference dye during that same incremental time period.

13. Apparatus for detecting the level of electrical activity in an area of living animal tissue dyed with both an electrically sensitive dye and an electrically insensitive dye, said dyes having different light emitting characteristics, comprising:

a main catheter;

an endoscope, positioned within said main catheter, with first and second optical fibers;

a light source optically connected to said endoscope for transmitting light through said endoscope's first optical fiber onto said area of dyed living animal tissue so that said area of dyed living animal tissue will emit responsive light to be passed through said endoscope's second optical fiber;

a beamsplitter optically connected to said endoscope to divide light passed through said endoscope's second optical fiber into a first light beam containing light characteristic of said electrically sensitive dye and a second light beam containing light characteristic of said electrically insensitive reference dye;

a first photodetector optically linked to said beamsplitter for detecting the intensity of light characteristic of said electrically sensitive dye;

a second photodetector optically linked to said beamsplitter for detecting the intensity of light characteristic of said electrically insensitive reference dye; and, a signal processor which receives intensity signals from said first and second photodetectors and then calculates the electrical activity in said area of living animal tissue in a way which discounts intensity signals attributable to tissue movement.

14. The apparatus of claim 13 wherein said light source is a laser.

15. The apparatus of claim 14 wherein said laser is an argon laser emitting blue-green light.

16. Apparatus for detecting the level of electrical activity in an area of living animal tissue dyed with both an electrically sensitive dye and an electrically insensitive dye, said dyes having different light emitting characteristics, comprising:

a main catheter, an endoscope, positioned within said main catheter, with first and second optical fibers;

an ablation catheter connected to said endoscope and positioned within said main catheter;

a light source optically connected to said endoscope for transmitting light through said endoscope's first optical fiber onto said area of dyed living animal tissue so that said area of dyed living animal tissue will emit responsive light to be passed through said endoscope's second optical fiber;

a beamsplitter optically connected to said endoscope to divide light passed through said endoscope's second optical fiber into a first light beam containing light characteristic of said electrically sensitive dye and a second light beam containing light characteristic of said electrically insensitive reference dye;

a first photodetector optically linked to said beamsplitter for detecting the intensity of light characteristic of said electrically sensitive dye;

a second photodetector optically linked to said beamsplitter for detecting the intensity of light characteristic of said electrically insensitive reference dye; and, a signal processor which receives intensity signals from said first and second photodetectors and then calculates the electrical activity in said area of living animal tissue in a way which discounts intensity signals attributable to tissue movement.

17. The apparatus of claim 13 further including a first set of lens and filters between said beamsplitter and said first photodetector and a second set of lens and filters between said beamsplitter and said second photodetector.

18. A method for detecting the level of electrical activity in an area of living animal tissue comprising:

infusing into said area of living animal tissue both an electrically sensitive dye and an electrically insensitive reference dye;

exciting said dyed tissue with incident light to cause said dyed tissue to emit light at a first wavelength characteristic of said electrically sensitive dye and a second wavelength characteristic of said electrically insensitive reference dye, detecting the intensity of light at both of said first and second wavelengths, calculating the electrical activity in said area of living animal tissue from the detected intensity of light at said first and second wavelengths in a way which discounts intensity signals attributable to tissue movement.

19. The method of claim 18 further including the step of displaying the calculated electrical activity in said area of living animal tissue.

20. The method of claim 18 further including the step of ablating any undesired tissue discovered as a result of calculating the electrical activity in said area of living animal tissue.

21. The method of claim 18 wherein said electrically sensitive dye is a styryl voltage sensitive dye.

22. The method of claim 18 wherein said electrically insensitive reference dye is tetramethirohodamine.

* * * * *